(12) United States Patent
Otis et al.

(10) Patent No.: US 8,870,370 B1
(45) Date of Patent: Oct. 28, 2014

(54) CONTACT LENS THAT FACILITATES ANTENNA COMMUNICATION VIA SENSOR IMPEDANCE MODULATION

(71) Applicants: Brian Otis, Sunnyvale, CA (US); Nathan Pletcher, Mountain View, CA (US)

(72) Inventors: Brian Otis, Sunnyvale, CA (US); Nathan Pletcher, Mountain View, CA (US)

(73) Assignee: Google Inc., Mountain View, CA (US)

( * ) Notice: Subject to any disclaimer, the term of this patent is extended or adjusted under 35 U.S.C. 154(b) by 212 days.

(21) Appl. No.: 13/625,835

(22) Filed: Sep. 24, 2012

(51) Int. Cl.
*G02C 7/00* (2006.01)
*A61B 3/00* (2006.01)
*G02C 7/04* (2006.01)

(52) U.S. Cl.
CPC ........................................ *G02C 7/04* (2013.01)
USPC ...................................... 351/159.03; 351/246

(58) Field of Classification Search
USPC ........................ 351/159.03, 159.39, 219, 246
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |
| 4,401,371 A | 8/1983 | Neefe | |
| 4,463,149 A | 7/1984 | Ellis | |
| 4,555,372 A | 11/1985 | Kunzler et al. | |
| 4,604,479 A | 8/1986 | Ellis | |
| 4,632,844 A | 12/1986 | Yanagihara et al. | |
| 4,686,267 A | 8/1987 | Ellis et al. | |
| 4,740,533 A | 4/1988 | Su et al. | |
| 4,826,936 A | 5/1989 | Ellis | |

(Continued)

FOREIGN PATENT DOCUMENTS

| | | |
|---|---|---|
| EP | 0369942 | 5/1990 |
| EP | 686372 | 12/1995 |

(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

(Continued)

*Primary Examiner* — Jack Dinh
(74) *Attorney, Agent, or Firm* — McDonnell Boehnen Hulbert & Berghoff LLP

(57) ABSTRACT

Systems, contact lenses and methods that facilitate antenna communication via sensor impedance modulation are provided. In one aspect, a system can include a contact lens and a radio frequency (RF) reader. The contact lens can include a substrate; an RF antenna, disposed on or within the substrate; and a sensing component, disposed on or within the substrate, and directly coupled to the RF antenna, wherein the RF antenna is configured to change impedance value as a sensed value of the sensing component changes. The RF reader is external to the contact lens, and configured to interrogate the RF antenna with an RF signal. The RF reader can receive a reflected RF signal from the RF antenna in response to the interrogation. The magnitude, phase and/or a frequency of the reflected RF signal can be based on the impedance value of the RF antenna.

19 Claims, 7 Drawing Sheets

(56) References Cited

U.S. PATENT DOCUMENTS

| | | |
|---|---|---|
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint |
| 5,177,165 A | 1/1993 | Valint et al. |
| 5,177,168 A | 1/1993 | Baron |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicholson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0234717 A1 | 9/2010 | Wismer |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0177576 A1 | 7/2012 | Hu |
| 2012/0201755 A1 | 8/2012 | Rozakis et al. |
| 2012/0245444 A1 | 9/2012 | Otis et al. |
| 2012/0259188 A1 | 10/2012 | Besling |

FOREIGN PATENT DOCUMENTS

| | | |
|---|---|---|
| EP | 1061874 | 12/2000 |
| EP | 1617757 | 1/2006 |
| EP | 1818008 | 8/2007 |
| EP | 1947501 | 7/2008 |

(56) References Cited

FOREIGN PATENT DOCUMENTS

| EP | 2457122 | 5/2012 |
|---|---|---|
| WO | 9504609 | 2/1995 |
| WO | 0116641 | 3/2001 |
| WO | 0134312 | 5/2001 |
| WO | 03065876 | 8/2003 |
| WO | 2004060431 | 7/2004 |
| WO | 2004064629 | 8/2004 |
| WO | 2006015315 | 2/2006 |
| WO | 2009094643 | 7/2009 |
| WO | 2010105728 | 9/2010 |
| WO | 2010133317 | 11/2010 |
| WO | 2011/011344 | 1/2011 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
Ho et al., "Contact Lens With Integrated Inorganic Semiconductor Devices," MEMS 2008. IEEE 21st International Conference on. IEEE, 2008., pp. 403-406.
Lähdesmäki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Parviz, Babak A., "For Your Eyes Only," IEEE Spectrum, Sep. 2009, pp. 36-41.
Saeedi, E et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.
Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.
Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.
Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Bionic contact lens 'to project emails before eyes,' http://www.kurzweilai.net/forums/topic/bionic-contact-lens-to-project-emails-before-eyes, Last accessed Mar. 14, 2012, 2 pages.
Tweedie, et al., "Contact creep compliance of viscoelastic materials via nanoindentation," J. Mater. Res., Jun. 2006, vol. 21, No. 2, pp. 1576-1589, Materials Research Society.
Brahim, et al., "Polypyrrole-hydrogel composites for the construction of clinically important biosensors," 2002, Biosensors & Bioelectronics, vol. 17, pp. 53-59.
Huang, et al., "Wrinkling of Ultrathin Polymer Films," Mater. Res. Soc. Symp. Proc., 2006, vol. 924, 6 pages, Materials Research Society.
Zarbin, et al., "Nanotechnology in ophthalmology," Can J Ophthalmol, 2010, vol. 45, No. 5, pp. 457-476.
Selner, et al., "Novel Contact Lens Electrode Array for Multi-electrode Electroretinography (meERG)," IEEE, 2011, 2 pages.
Liao, et al., "A 3-µW CMOS Glucose Sensor for Wireless Contact-Lens Tear Glucose Monitoring," IEEE Journal of Solid-State Circuits, Jan. 2012, vol. 47, No. 1, pp. 335-344.
Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.
Thomas, et al., "Functional Contact Lenses for Remote Health Monitoring in Developing Countries," IEEE Global Humanitarian Technology Conference, 2011, pp. 212-217, IEEE Computer Society.
Pandey, et al., "A Fully Integrated RF-Powered Contact Lens With a Single Element Display," IEEE Transactions on Biomedical Circuits and Systems, Dec. 2010, vol. 4, No. 6, pages.
Lingley, et al., "Multipurpose integrated active contact lenses," SPIE, 2009, 2 pages.
Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.
Liao, et al., "A 3µW Wirelessly Powered CMOS Glucose Sensor for an Active Contact Lens," 2011 IEEE International Solid-State Circuits Conference, Session 2, Feb. 21, 2011, 3 pages.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Lončar, et al., "Design and Fabrication of Silicon Photonic Crystal Optical Waveguides," Journal of Lightwave Technology, Oct. 2000, vol. 18, No. 10, pp. 1402-1411.
Liu, et al., "Miniature Amperometric Self-Powered Continuous Glucose Sensor with Linear Response," Analytical Chemistry, 7 pages.
Baxter, "Capacitive Sensors," 2000, 17 pages.
Lingley, et al., "A Single-Pixel Wireless Contact Lens Display," Journal of Micromechanics and Microengineering, 2011, 9 pages.
"Polyvinylidene fluoride," Wikipedia, http://en.wikipedia.org/wiki/Polyvinylidene_fluoride, Last accessed Mar. 30, 2012, 4 pages.
Murdan, "Electro-responsive drug delivery from hydrogels," Journal of Controlled Release, 2003, vol. 92, pp. 1-17.

(56) References Cited

OTHER PUBLICATIONS

Haders, "New Controlled Release Technologies Broaden Opportunities for Ophthalmic Therapies," Drug Delivery Technology, Jul./Aug. 2009, vol. 8, No. 7, pp. 48-53.
Singh, et al., "Novel Approaches in Formulation and Drug Delivery using Contact Lenses," Journal of Basic and Clinical Pharmacy, May 2011, vol. 2, Issue 2, pp. 87-101.
"Contact Lenses: Look Into My Eyes," The Economist, Jun. 2, 2011, http://www.economist.com/node/18750624/print, Last accessed Mar. 13, 2012, 8 pages.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.
Unpublished U.S. Appl. No. 13/240,994, Titled "See-Through Display With Infrared Eye-Tracker," filed Sep. 22, 2011, 38 pages.
Unpublished U.S. Appl. No. 13/209,706, Titled "Optical Display System and Method with Gaze Tracking," filed Aug. 15, 2011, 30 pages.
Adler, "What types of statistical analysis do scientists use most often?" O'Reilly Community, Jan. 15, 2010, 2 pages, http://broadcast.oreilly.com/2010/01/what-types-of-statistical-anal.html, Last accessed Sep. 4, 2012.
Bull, "Different Types of Statistical Analysis," Article Click, Feb. 4, 2008, 4 pages, http://www.articleclick.com/Article/Different-Types-Of-Statistical-Analysis/968252, Last accessed Sep. 4, 2012.
"Understanding pH measurement," Sensorland, 8 pages, http://www.sensorland.com/HowPage037.html, Last accessed Sep. 6, 2012.
"Regression analysis," Wikipedia, 11 pages, http://en.wikipedia.org/wiki/Regression_analysis, Last accessed Sep. 6, 2012.
"Statistics," Wikipedia, 10 pages, http://en.wikipedia.org/wiki/Statistics, Last accessed Sep. 6, 2012.
"Nonlinear regression," Wikipedia, 4 pages, http://en.wikipedia.org/wiki/Nonlinear_regression, Last accessed Sep. 10, 2012.
"Linear regression," Wikipedia, 15 pages, http://en.wikipedia.org/wiki/Linear_regression, Last accessed Sep. 10, 2012.
"Integrated circuit," Wikipedia, 9 pages, http://en.wikipedia.org/wiki/Integrated_circuit, Last accessed Sep. 10, 2012.
"Photolithography," Wikipedia, 8 pages, http://en.wikipedia.org/wiki/Photolithography, Last accessed Sep. 10, 2012.
"Alcohol Detection Technologies: Present and Future," American Beverage Institute, 9 pages.
Harding, et al., "Alcohol Toxicology for Prosecutors: Targeting Hardcore Impaired Drivers," American Prosecutors Research Institute, Jul. 2003, 40 pages.
Kim, et al., "Oral Alcohol Administration Disturbs Tear Film and Ocular Surface," American Academy of Ophthalmology, 2012, 7 pages.
Quick, "Color-changing electrochromic lens technology has fashion and military applications," Gizmag, Jul. 12, 2011, http://www.gizmag.com/electrochromic-lens-technology/19191/, Last accessed Apr. 12, 2012, 4 pages.
Chu, "Contact Lenses that Respond to Light," Technology Review, Nov. 10, 2009, http://www.technologyreview.com/printer_friendly_article.aspx?id=23922, Last accessed Apr. 12, 2012, 2 pages.

CONTACT LENS THAT FACILITATES ANTENNA COMMUNICATION VIA SENSOR IMPEDANCE MODULATION

TECHNICAL FIELD

This disclosure generally relates to a contact lens that facilitates antenna communication via sensor impedance modulation.

DETAILED DESCRIPTION

Figure 1:
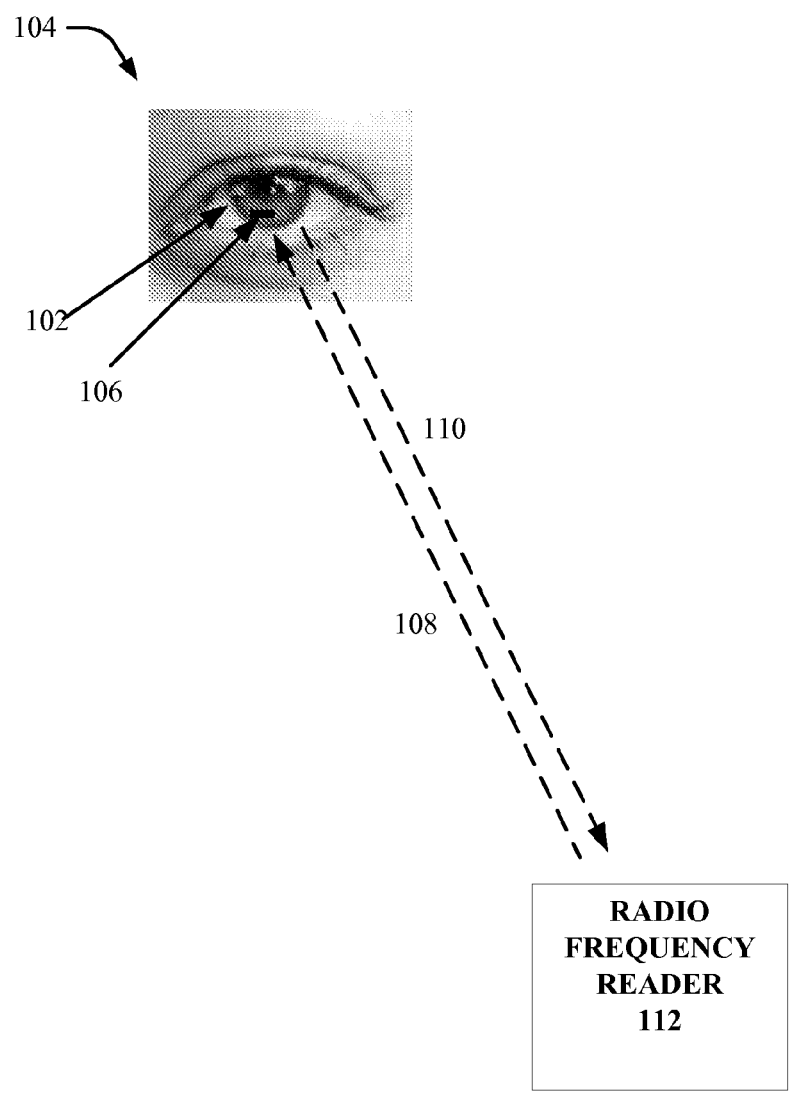
FIG. 1 illustrates a system that includes an exemplary non-limiting contact lens that facilitates antenna communication via sensor impedance modulation in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

In these aspects described herein, apparatus, systems and methods relate to contact lenses that facilitate antenna communication. For example, a contact lens includes a sensor and an antenna directly coupled to one another. The antenna is an electrically short antenna and, as such, the capacitance, inductance or resistance change in the sensor results in a change in impedance in the antenna. The change in impedance is related to the amount of the change in capacitance, inductance or resistance at the sensor. The antenna can receive a radio frequency (RF) interrogation signal from an RF reader external to the contact lens, and can reflect a version of the RF interrogation signal. The reflected version of the RF interrogation signal can have a magnitude, phase and/or frequency that is distinct from that of the RF interrogation signal. The modification in the reflected version can be a result of the impedance of the antenna. As such, the RF reader can receive a signal that is modified and, based on the modification, determine the amount of a feature sensed by the sensor.

The aspects described herein enable communication of contact lens sensor information from an antenna on the contact lens with minimal circuitry (because no integrated circuits are employed for reading out the current of the contact lens sensor). Additionally, there are no integrated circuits that are employed for reading out voltage, charge, capacitance or impedance, each of which could be a varying output of the sensor in various aspects described herein. Thus, power consumption and complexity of the contact lens are minimized relative to systems that require integrated circuitry to read out sensor current, voltage, charge, capacitance or impedance.

An antenna is composed of metallic conductors electrically connected to a receiver or transmitter. An oscillating current of electrons forced through the antenna by a transmitter creates an oscillating magnetic field around conductors of the antenna. The charge of oscillating electrons creates an oscillating electric field along the conductors. The fields radiate from the antenna into space as electromagnetic waves. During reception, oscillating electric and magnetic fields of incoming radio waves exert force on electrons in the antenna conductors and cause the conductors to generate oscillating currents in the antenna. Accordingly, an antenna converts radio waves into electric power (and vice versa).

Antennas can be omni-directional and transmit or receive radio waves in all directions equally, or directional, and transmit and receive radio waves in a beam toward and from a predefined direction.

Impedance of an antenna is derived from voltage and current at an input to the antenna. For complex impedance, the real part of the impedance represents power radiated away or absorbed within the antenna. An imaginary part of the impedance represents power stored in a near field of the antenna, and is non-radiated power. An antenna with only real input impedance (zero imaginary input to the impedance) is resonant. Impedance of an antenna varies with frequency.

Apparatus, systems and methods disclosed herein relate to contact lenses that facilitate antenna communication via sensor impedance modulation. In various aspects, a system can include a contact lens and an RF reader. The contact lens can include: a substrate; an RF antenna, disposed on or within the substrate; and a sensing component, disposed on or within the substrate, and directly coupled to the RF antenna, wherein the RF antenna is configured to change impedance value as a sensed value of the sensing component changes In another aspect, a system can include a contact lens and an RF reader. The contact lens can include: a substrate; a capacitive pressure sensing component disposed on or within the substrate; and an RF antenna, directly coupled to the capacitive pressure sensing component, and configured to modify a reflected version of a received RF signal at a selected frequency based, at least, on the information sensed by the capacitive pressure sensing component.

In another aspect, a method can include: sensing, on a contact lens, one or more features associated with a wearer of the contact lens; changing an impedance value based, at least, on a change in a value associated with the one or more sensed features; and transmitting a radio frequency (RF) signal, wherein the RF signal is based, at least, on using the change in the impedance value.

Turning first to FIG. 1, a system 100 is illustrated that includes an exemplary non-limiting contact lens that facilitates antenna communication via sensor impedance modulation in accordance with aspects described herein. The system 100 includes a contact lens 102 covering at least a portion of an eye 104, and a radio frequency (RF) reader 112.

The contact lens 102 can sense one or more different features (e.g., temperature at the contact lens 102, object in proximity to the contact lens 102) associated with a wearer of the contact lens 102, and communicate via an RF signal transmitted to the RF reader 112. For example, the contact lens 102 can include one or more components (represented by component 106). In various aspects, the one or more component 106 can include a capacitive, inductive or resistive sensing component (not shown) and an RF antenna on the contact lens 102. The RF antenna can be directly coupled to the sensing component.

For example, the sensing component can be a capacitive pressure sensor that changes capacitance when pressure across the contact lens 102 changes. As another example, the sensing component can be a capacity proximity sensor that changes capacitance based on proximity of material or fluid to the sensing component. For example, the sensing component can include two conductive plates, spaced apart from one another and material (e.g., dielectric) between the surfaces of the conductors. A change in distance between conductive surfaces or proximity of material or fluid near conductive surfaces can cause change of capacitance due to change in electric field associated with the conductive surfaces. Further, because materials emitted from an eye region are in proximity to a contact lens 102 over the eye 104, capacitive sensors on the contact lens 102 can change capacitance based on change in electric field when materials approach the contact lens 102. Similarly, fingers and other objects can change capacitance on a contact lens 102. The sensing component can detect capacitance on the contact lens 102 in these scenarios, for example.

As another example, the sensing component can be a temperature sensor that changes resistance based on sensed temperature. For example, the sensing component can include a resistance component (e.g., resistance thermometer) that senses temperature on the contact lens 102 and increases resistance with a rise in temperature or decreases in resistance with a decrease in temperature.

The sensing component can be directly coupled to the RF antenna. As such, and based on the RF antenna design as an electrically short antenna, a change in capacitance, inductance or resistance at the sensing component can cause change in impedance in an RF antenna.

The RF reader 112 can transmit an RF signal 108 to the contact lens 102 to interrogate the contact lens 102 for information associated with sensed features. Upon receiving the RF signal, the antenna can transmit a reflected RF signal 110 back to the RF reader 112. In various aspects, the reflected RF signal 110 can be a modified version of the RF signal 108. Specifically, the magnitude, phase and/or frequency of the RF signal 108 can be modified based on impedance of the antenna.

The RF reader 112 can compare the received, reflected RF signal 110 with the RF signal 108 to determine impedance of the antenna. In some aspects, the RF reader 112 can evaluate magnitude, phase and/or frequency of the reflected RF signal 110 to determine impedance of the antenna. For example, the RF reader 112 can interrogate the contact lens 102 with a burst of RF signal and then listen for a reflected signal. A resonator on the contact lens 102 would continue to vibrate at its resonant frequency. Thus, the RF reader 112 can listen for a separate frequency that is distinct from the frequency of the transmitted RF signal.

The RF reader 112 can then compare impedance of the antenna (or the received magnitude, phase and/or frequency of the reflected RF signal) to information linking the impedance (or received magnitude, phase and/or frequency) with a sensed value. As such, the contact lens 102 can sense features on the contact lens 102 and communicate the sensed information via impedance modulation of the antenna (as caused by the sensing component).

Various aspects of the contact lens that facilitate antenna communication via sensor impedance modulation will be described with reference to FIGS. 2A, 2B and 2C. These figures illustrate exemplary non-limiting contact lenses that facilitate antenna communication via sensor impedance modulation in accordance with aspects described herein.

Contact lens 102 can be as shown and/or described with reference to FIGS. 2A, 2B and 2C. One or more of the respectively depicted contact lenses 200, 210, 220 can include structure and/or functionality of contact lens 102 (and vice versa).

Figure 2A:
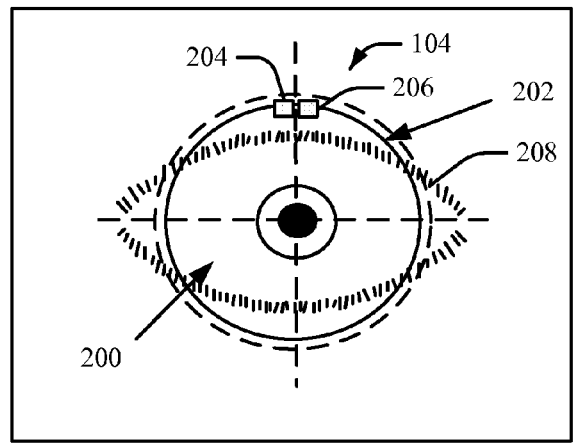
FIGS. 2A, 2B and 2C illustrate exemplary non-limiting contact lenses that facilitate antenna communication via sensor impedance modulation in accordance with aspects described herein.

Turning first to FIG. 2A, contact lens 200 can include a substrate 202, a sensing component 204 and an antenna 206. One or more portions of the substrate 202 can be transparent and/or translucent in various aspects. In various aspects, the substrate is formed to cover at least a portion of the eye 104.

The sensing component 204 and/or antenna 206 can be disposed on or within the substrate 202. While the sensing component 204 and the antenna 206 are shown near a top portion of the substrate 202 in FIG. 2A, in various aspects, the sensing component 204 and the antenna 206 can be positioned in any suitable location on the substrate 202. For example, the sensing component 204 and the antenna 206 can be located proximate to a portion of the substrate 202 covering a pupil of the eye 104.

The sensing component 204 can be directly coupled to the antenna 206 in some aspects. In various aspects, the sensing component 204 being directly coupled to the antenna 206 means that the sensing component 204 is molded to the antenna 206 and/or that only a wire connects the sensing component 204 and the antenna 206 (with no other intervening components). In some aspects, the sensing component 204 and antenna 206 can be fabricated through multi-stage injection molding to join such dissimilar materials to one another and/or to the substrate 202.

In various aspects, the sensing component 204 can be an inductive, capacitive or resistive sensing component. The sensing component 204 can be configured to sense any suitable number of different features associated with a wearer of the contact lens 200. For example, sensing component 204 can be configured such that inductance, capacitance or resistance changes as the feature is sensed. As the inductance, capacitance and/or resistance of the sensing component 204 changes, impedance 206 (real impedance, complex impedance or real and complex impedance) of the antenna 206 correspondingly changes.

For example, the sensing component 204 can be configured to sense temperature of a body of the wearer of the contact lens 200. Resistance of the sensing component 204 can change as sensed temperature changes. Accordingly, with change in resistance, impedance of the antenna 206 correspondingly changes. As such, impedance of the antenna 206 can be an indicator of value (or relative value) of the sensed feature.

As another example, the sensing component 204 can be a biosensor configured to detect level of glucose, lactate, hydrogen ions and/or urea in a body of the wearer of the contact lens 200. For example, the sensing component 204 can be configured to generate electrical current upon sensing glucose, lactate, hydrogen ions and/or urea (and/or a predefined level thereof). The generated current modifies impedance of the antenna 206.

Also, in various aspects, the voltage, charge, capacitance or impedance of the sensing component 204 can change upon sensing glucose, lactate, hydrogen ions and/or urea (and/or a predefined level thereof). The change in voltage, charge, capacitance or impedance of the sensing component 204 can modify the impedance of the antenna 206. As an example, the sensing component 204 can be a capacitive sensor having two capacitor plates in proximity to one another. The sensing component 204 can detect or measure proximity of an object (e.g., eyelid 208) to the sensing component 204 on the contact lens 200, humidity on the contact lens 200 and/or fluid level on the contact lens 200. Because biological materials emitted from the eye 104 are in proximity to the contact lens 200 over the eye 104, a capacitive sensor on the contact lens can change capacitance based on change in electric field when biological materials approach the contact lens 200. Similarly, fingers and other objects can change capacitance on a contact lens 200.

As another example, the sensing component 204 can be a capacitive pressure sensor that detects pressure across the contact lens 200, and changes capacitance in accordance with the detected pressure.

In the above two capacitive sensing aspects, the sensing component 204 can be a capacitive sensor that changes capacitance with sensed proximity and/or pressure. The change in capacitance can cause change in impedance of the antenna 206.

In aspects of the sensing component 204 described above, the sensing component 204 requires no electrical power to operate. Instead of capacitance, for example, being read out by active circuitry on the contact lens 200, the sensing component 204 can be coupled to antenna 206 on the contact lens 200. The antenna 206 can resonate at a particular frequency based on impedance of the sensing component 204.

The antenna 206 can be an electrically short antenna. As such, capacitance, inductance or resistance of the sensing component 204 can affect impedance in the antenna 206. In some aspects, the antenna 206 can be an RF antenna configured to receive an RF interrogation signal from an interrogation device (e.g., RF reader 112) external to the contact lens 200. The antenna 206 can reflect a modified RF signal back to the interrogation device. In some aspects, the reflected RF signal can be modified at a selected resonance frequency.

The magnitude, phase and/or frequency of the reflected RF signal from the antenna 206 can be a function of impedance of the antenna 206. Specifically, the modified RF reflected signal can be a function of loading on the antenna 206 from the sensing component 204. Based on amount of RF reflected signal, the RF reader can determine data and/or values of features sensed by the sensing component 204 without need for active electronics (other than the sensing component 204 and antenna 206) on the contact lens 200.

Accordingly, in some aspects, the contact lens 200 (and systems including the contact lens 200 and RF reader 112, such as that described with reference to FIG. 1) can remotely and wirelessly read out a signal generated by an antenna 206. In lieu of an integrated circuit to actively read out an output from the sensing component 204, the sensing component 204 can modulate impedance of the antenna 206 that is on the contact lens 200 to communicate value of the sensed feature.

The RF reader 112 can determine value of the feature sensed by the sensing component 204 by comparing magnitude, phase and/or frequency of the reflected RF signal with magnitude, phase and/or frequency information stored in the RF reader 112 or in a data storage location accessible by the RF reader 112. For example, the RF reader 112 can compare magnitude, phase and/or frequency having a first set of values (or being within a first range of magnitude, phase and/or frequency values) with stored information. The RF reader 112 can determine value of sensed capacitance or sensed temperature, for example, by locating sensed values that correspond to magnitude, phase and/or frequency of the reflected RF signal from the antenna 206.

The simplicity of the contact lens 200 can enable sensed information to be read remotely and wirelessly from the contact lens 200 while maintaining a simple contact lens 200 that requires no integrated circuit to read out sensed information/values/data from the sensing component 204.

Figure 2B:
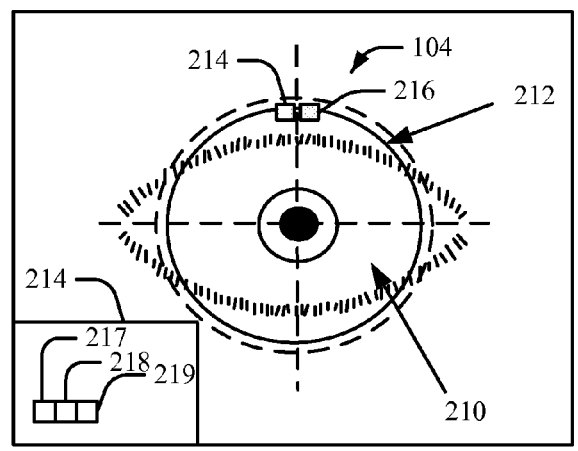

Turning now to FIG. 2B, similar to the contact lens 200, contact lens 210 can include a substrate 212, a sensing component 214 and an antenna 216. The sensing component 214 and/or antenna 216 can be disposed on or within the substrate 212 and can be positioned at any suitable location on or within the substrate 212.

As described with reference to FIG. 2A, the sensing component 214 can be configured to sense any suitable number of different features associated with the wearer of the contact lens 210. Distinct from sensing component 204, however, sensing component 214 can include a plurality of sensors 217, 218, 219 that can sense two or more different features on the contact lens 210. In some aspects, sensors 217, 218, 219 can be an array of sensors as shown in FIG. 2B. In other aspects, the sensors 217, 218, 219 are each directly coupled to antenna 216 but are disparate and distinct from one another.

The sensors 217, 218, 219 can be inductive, capacitive or resistive sensors that change inductance, capacitance or resistance as different features are sensed by sensors 217, 218, 219. As inductance, capacitance and/or resistance changes, contribution of impedance of the antenna 216 by the sensors 217, 218, 219 changes. Accordingly, the different sensors 217, 218, 219 can cause the antenna 216 to have different impedances depending on respective features sensed by the sensors. As with the sensing component 204, real impedance, complex impedance or real and complex impedance can change as value of the sensed feature changes.

Each of the sensors 217, 218, 219 can be directly coupled to the antenna 216 and, in some aspects, the sensors 217, 218, 219 and antenna 216 can be fabricated through multi-stage injection molding to join dissimilar materials to one another.

As described with reference to FIG. 2A, the antenna 216 can be an electrically short antenna that can resonate at a particular frequency based on impedance of the antenna 216. In this aspect, the antenna 216 can be configured to modify a reflected RF signal based on impedance of the antenna 216, which can vary based on the output of sensors 217, 218, 219. In various different aspects, the outputs of the sensors 217, 218, 219 can be any number of different electrical parameters that change the impedance of antenna 216. By way of example, but not limitation, the outputs of the sensors 217, 218, 219 that can change the impedance of the antenna 216 can be current, voltage, charge, capacitance, impedance or the like.

For example, the antenna 216 can be interrogated with an RF signal of a particular resonance frequency associated with a particular sensor of sensors 217, 218, 219. As such, when the RF antenna receives an RF signal of a resonance frequency associated with sensor 217, for example, the antenna 216 can reflect an RF signal having magnitude, phase and/or frequency indicative of impedance of the antenna 216 caused by sensor 217. Similarly, when the antenna 216 receives an RF signal of a resonance frequency associated with sensor 218, the antenna 216 can reflect an RF signal having magnitude, phase and/or frequency indicative of the impedance of the antenna 216 caused by sensor 218. The RF reader can receive the reflected signal.

The contact lens 210 can therefore be interrogated in the frequency domain, and change in RF signal (between the original RF signal and the reflected RF signal) can be evaluated by the RF reader in the frequency domain to determine values of features sensed on the contact lens 210.

As such, aspects described herein can enable multiple sensors (e.g., sensors 217, 218, 219) on the contact lens 210 that can be configured to perform sensing of different features and the contact lens 210 can communicate the sensed features via modified reflected RF signals.

Figure 2C:
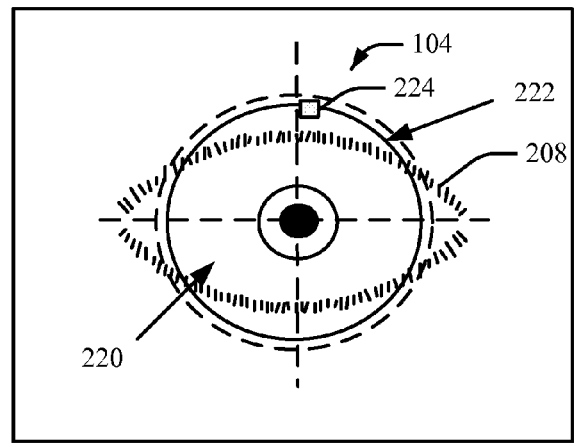

Turning now to FIG. 2C, in some aspects, the contact lens 220 can include a substrate 222 and an antenna 224. The antenna 224 can be configured to perform sensing of one or more features on the contact lens 220. For example, the antenna 224 can include a piezoelectric resonator that changes its resonant frequency based on the sensed feature (e.g., temperature of the wearer of the contact lens 220) or based on sensed deformation of a material on the contact lens 220 (similar to a strain gauge). Rather than generating a voltage with piezoelectric material, the changing resonant frequency of the material would be detectable as a change in the reflected RF signal from the RF reader. The piezoelectric material can include, but is not limited to, any suitable number of suitable biocompatible materials. For example, the material can include a piezoelectric ceramic and/or polyvinylidene fluoride (PVDF). The change in resonant frequency due to the sensed feature can be detected as a change in the frequency response of the impedance of antenna 224. The magnitude and/or phase of the reflected signal can then vary based on the varying impedance of the antenna 224.

Although not required and not shown in FIGS. 2A, 2B and 2C, in some aspects, one or more of the contact lenses 102, 200, 210, 220 can include a memory and/or microprocessor. The memory can store information regarding the features sensed by the sensing component 204, 214 (or by antenna 224 in contact lens 220). In some aspects, the memory can store computer-executable instructions for execution by the microprocessor. The microprocessor can execute computer-executable instructions to perform one or more functions of the contact lens 102, 200, 210, 220.

Figure 3:
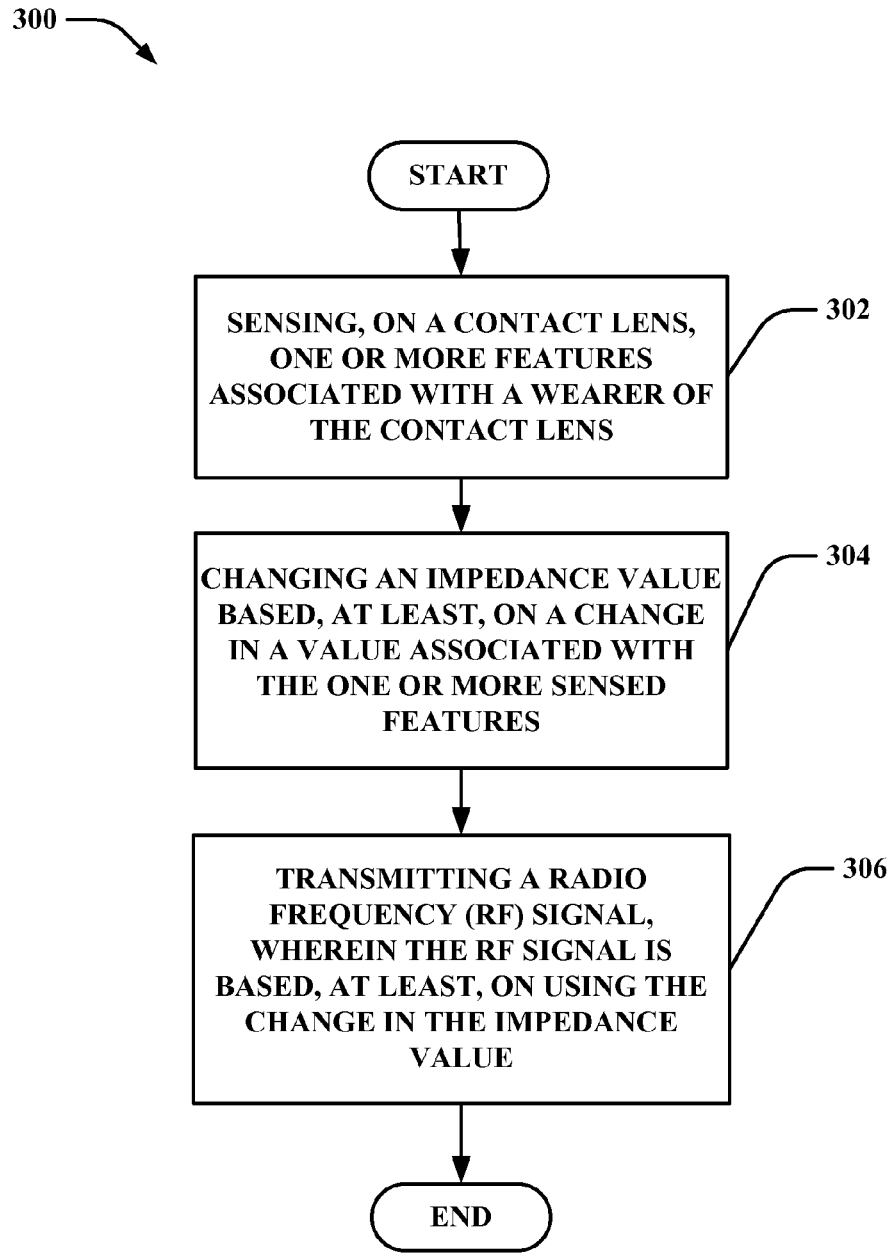
FIGS. 3, 4 and 5 are illustrations of exemplary non-limiting flow diagrams of methods that facilitate communication via contact lens sensor impedance modulation in accordance with aspects described herein.
Figure 4:
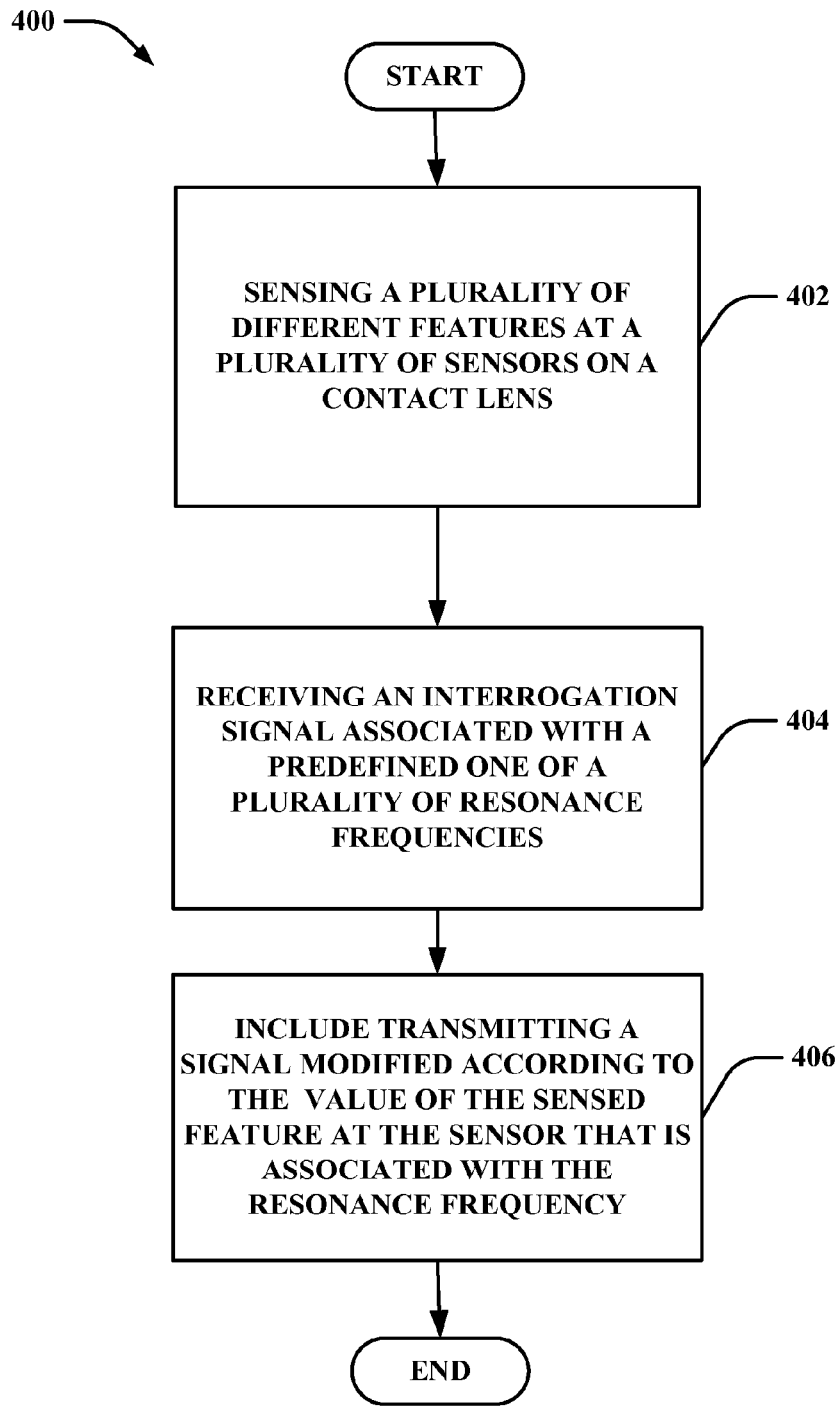
Figure 5:
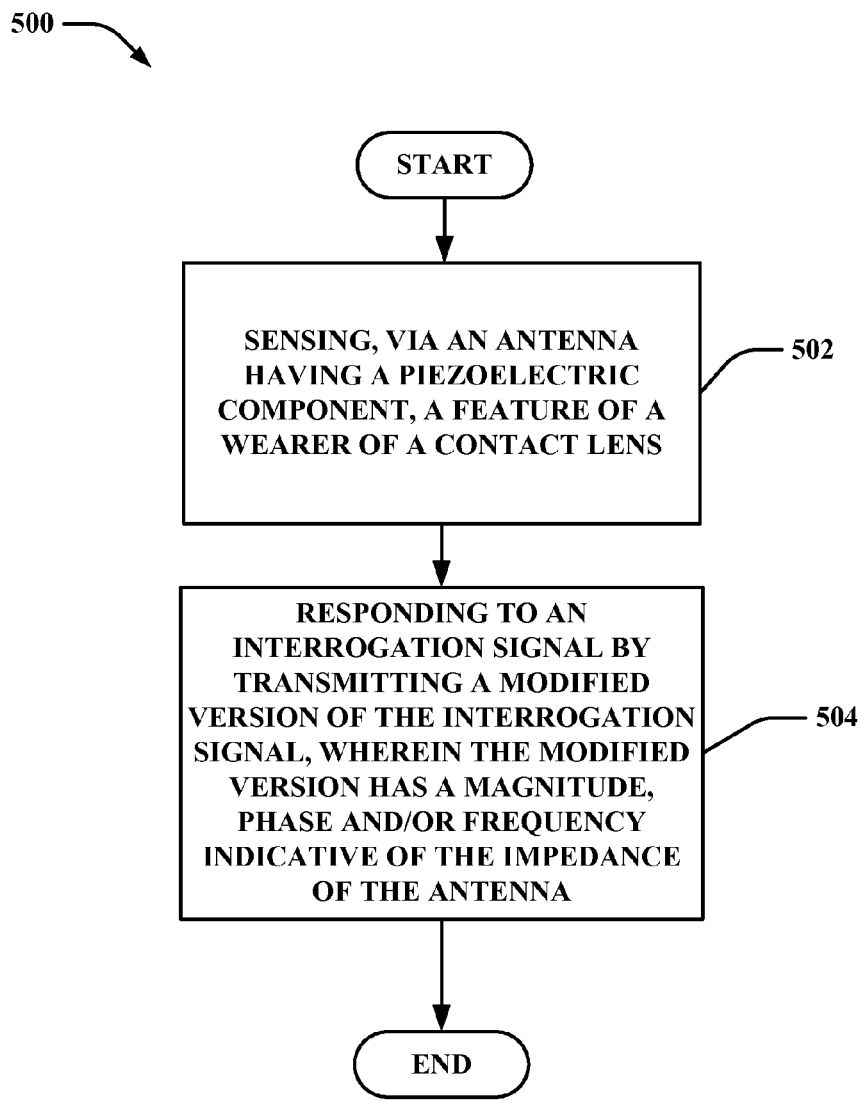

FIGS. 3, 4 and 5 are illustrations of exemplary non-limiting flow diagrams of methods that facilitate communication via contact lens sensor impedance modulation in accordance with aspects described herein.

Turning first to FIG. 3, at 302, method 300 can include sensing, on a contact lens, one or more features associated with a wearer of the contact lens (e.g., using the contact lens 102, 200, 210, 220 and/or sensing component 204, 214). The sensing component 204 can be configured to sense any suitable number of different features (e.g., temperature of a wearer of the contact lens, capacitance across the contact lens). The sensing can be performed by an inductive, capacitive or resistive sensing component.

At 304, method 300 can include changing an impedance value based, at least, on a change in a value associated with the one or more sensed features (e.g., using the antenna 206, 216, 224). The impedance value that can change can be the impedance of an electrically short RF antenna directly coupled to the sensing component. The sensing component can be configured such that the inductance, capacitance or resistance changes as the feature is sensed. As the inductance, capacitance and/or resistance of the sensing component changes, the impedance (real impedance, complex impedance or real and complex impedance) of the antenna correspondingly changes.

At 306, method 300 can include transmitting an RF signal, wherein the RF signal is based, at least, on using the change in the impedance value (e.g., using the antenna 206, 216, 224). The RF signal can be a reflected version of an RF signal received from an interrogation device, for example. The RF signal that is reflected can be reflected in response to receipt of the interrogation signal at the antenna. The impedance of the antenna can determine the magnitude, phase and/or frequency of the reflected RF signal.

Turning now to FIG. 4, at 402, method 400 can include sensing a plurality of different features at a plurality of sensors on a contact lens (e.g., using sensors 217, 218, 219). The sensors can be respectively associated with different resonance frequencies. The features sensed can include, but are not limited to, temperature, proximity to a sensor (e.g., via capacitive proximity sensing) and/or pressure on a sensor (e.g., via capacitive pressure sensing). In various aspects, the sensors 217, 218, 219 can each be directly coupled to an RF antenna on the contact lens.

At 404, method 400 can include receiving an interrogation signal associated with a predefined one of a plurality of resonance frequencies (e.g., using the antenna 206, 216). The interrogation signal can be an RF signal received from an RF reader external to the contact lens, for example.

At 406, method 400 can include transmitting a signal modified according to the value of the sensed feature at the sensor that is associated with the resonance frequency (e.g., using the antenna 206, 216). The impedance can be the impedance of an antenna directly coupled to an inductive, capacitive or resistive sensing component. The inductance, capacitance or resistance of the sensing component alters the impedance of the antenna. Accordingly, the signal transmitted by the antenna is a function of the inductance, capacitance, resistance of the sensing component. Upon receipt of an RF interrogation signal, the antenna transmits a reflected version of the RF signal. The reflected version is a function of the impedance of the antenna. As such, the magnitude, phase and/or frequency of the reflected RF signal can be a function of the impedance of the antenna (which is a function of the inductance, capacitance and/or resistance of the sensing component).

Turning now to FIG. 5, at 502, method 500 can include sensing, via an antenna having a piezoelectric component, a feature of a wearer of a contact lens (e.g., using antenna 224). The antenna can include a resonator, for example, composed of piezoelectric material. The resonant frequency of the piezoelectric material can change based on temperature and/or deformation of a material on the contact lens.

Although not shown, in other aspects, in lieu of changing resonant frequency of a resonator based on the value of a sensed feature, a method could include modulating the impedance of the antenna based on the value of a sensed feature (e.g., using the antenna 224).

At 504, method 500 can include responding to an interrogation signal by transmitting a modified version of the interrogation signal, wherein the modified version has a magnitude, phase and/or frequency indicative of the impedance of the antenna (e.g., using the antenna 224).

Exemplary Networked and Distributed Environments

Figure 6:
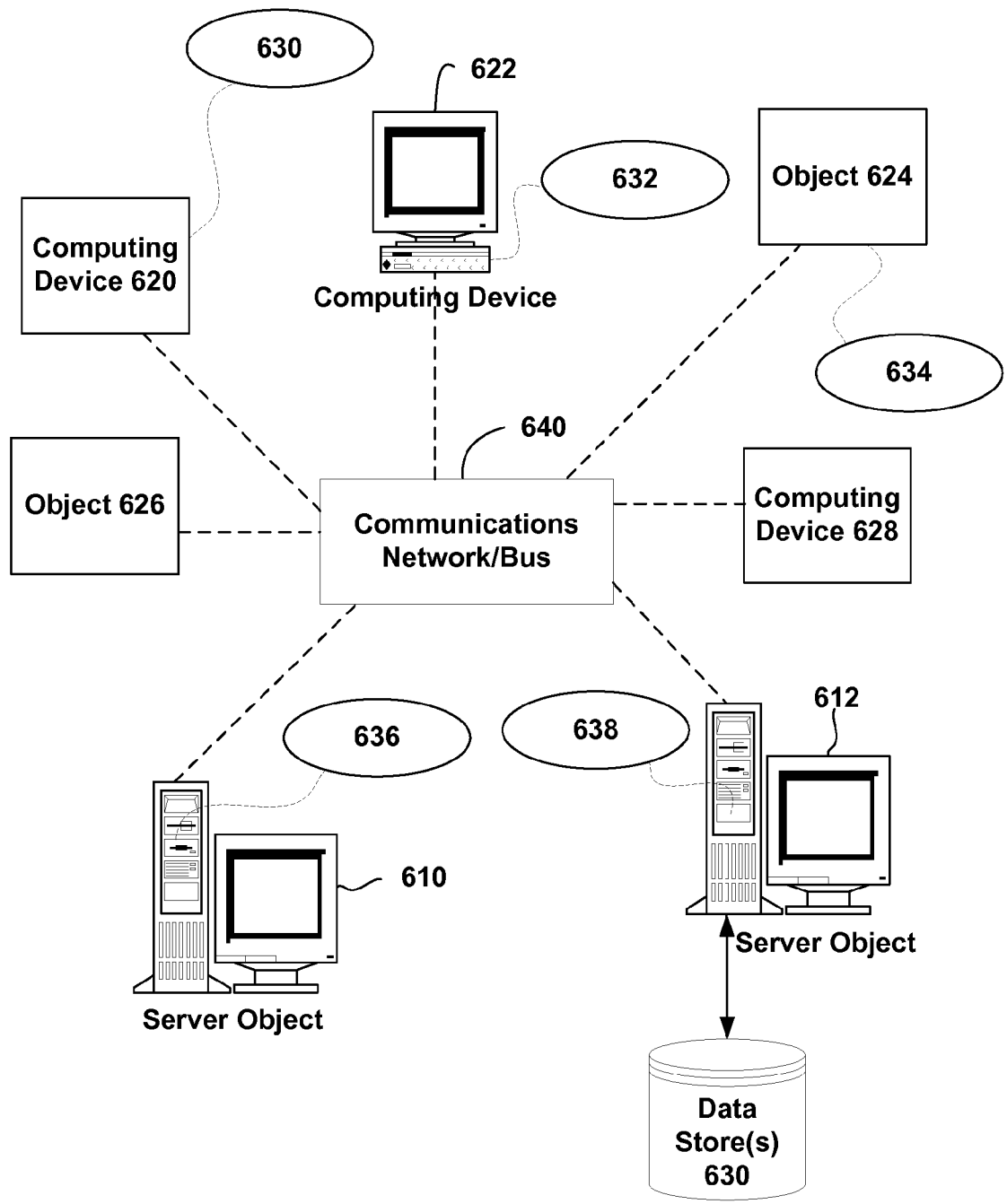
FIG. 6 is an illustration of a schematic diagram of an exemplary networked or distributed computing environment with which one or more aspects described herein can be associated.

FIG. 6 provides a schematic diagram of an exemplary networked or distributed computing environment with which one or more aspects described in this disclosure can be associated. The distributed computing environment includes computing objects 610, 612, etc. and computing objects or devices 620, 622, 624, 626, 628, etc., which can include programs, methods, data stores, programmable logic, etc., as represented by applications 630, 632, 634, 636, 638. It can be appreciated that computing objects 610, 612, etc. and computing objects or devices 620, 622, 624, 626, 628, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 610, 612, etc. and computing objects or devices 620, 622, 624, 626, 628, etc. can communicate with one or more other computing objects 610, 612, etc. and computing objects or devices 620, 622, 624, 626, 628, etc. by way of the communications network 640, either directly or indirectly. Even though illustrated as a single element in FIG. 6, network 640 can include other computing objects and computing devices that provide services to the system of FIG. 6, and/or can represent multiple interconnected networks, which are not shown.

In a network environment in which the communications network/bus 640 can be the Internet, the computing objects 610, 612, etc. can be Web servers, file servers, media servers, etc. with which the client computing objects or devices 620, 622, 624, 626, 628, etc. communicate via any of a number of known protocols, such as the hypertext transfer protocol (HTTP).

Exemplary Computing Device

As mentioned, advantageously, the techniques described in this disclosure can be associated with any suitable device. As described, in some aspects, the device can be the contact lens (or components of the contact lens) described herein. In various aspects, the data store can include or be included within any of the memory or RF readers described herein. In various aspects, the data store can be any repository for storing information transmitted to or received from the contact lens.

Figure 7:
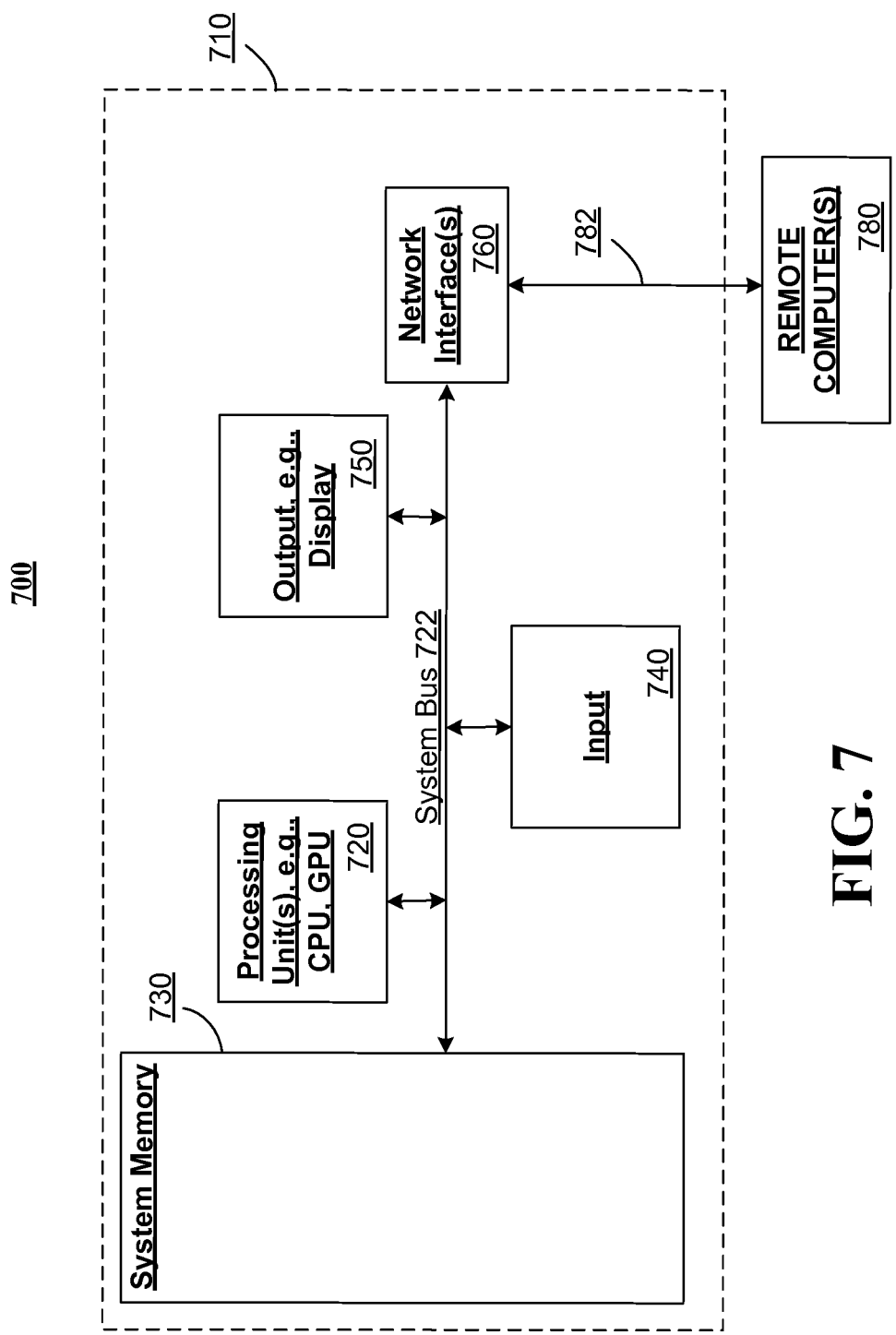
FIG. 7 is an illustration of a schematic diagram of an exemplary computing environment with which one or more aspects described herein can be associated.

FIG. 7 illustrates an example of a suitable computing system environment 700 in which one or aspects of the aspects described in this disclosure can be implemented. Components of computer 710 can include, but are not limited to, a processing unit 720, a system memory 730, and a system bus 722 that couples various system components including the system memory to the processing unit 720.

Computer 710 typically includes a variety of computer readable media and can be any available media that can be accessed by computer 710. The system memory 730 can include computer storage media in the form of volatile and/or nonvolatile memory such as read only memory (ROM) and/or random access memory (RAM). By way of example, and not limitation, memory 730 can also include an operating system, application programs, other program components, and program data.

A user can enter commands and information into the computer 710 through input devices 740 (e.g., keyboard, keypad, a pointing device, a mouse, stylus, touchpad, touch screen, motion detector, camera, microphone or any other device that allows the user to interact with the computer 710). A monitor or other type of display device can be also connected to the system bus 722 via an interface, such as output interface 750. In addition to a monitor, computers can also include other peripheral output devices such as speakers and a printer, which can be connected through output interface 750.

The computer 710 can operate in a networked or distributed environment using logical connections to one or more other remote computers, such as remote computer 780. The remote computer 780 can be a personal computer, a server, a router, a network PC, a peer device or other common network node, or any other remote media consumption or transmission device, and can include any or all of the elements described above relative to the computer 710. The logical connections depicted in FIG. 7 include a network 782, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and nonvolatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory or contact lens (or components thereof) described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

As used in this application, the terms "component," "component," "system," and the like are intended to refer to a computer-related entity, either hardware, software, firmware, a combination of hardware and software, software and/or software in execution. For example, a component can be, but is not limited to being, a process running on a processor, a processor, an object, an executable, a thread of execution, a program, and/or a computer. By way of illustration, both an application running on a computing device and/or the computing device can be a component. In addition, components can execute from various computer-readable storage media having various data structures stored thereon. The components can communicate by way of local and/or remote processes such as in accordance with a signal having one or more data packets (e.g., data from one component interacting with another component in a local system, distributed system, and/or across a network such as the Internet with other systems by way of the signal).

The word "exemplary" is used herein to mean serving as an example, instance, or illustration. For the avoidance of doubt, the subject matter disclosed herein is not limited by such examples. In addition, any aspect or design described in this disclosure as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A system, comprising:
   a contact lens, comprising:
      a substrate;
      a radio frequency (RF) antenna, disposed on or within the substrate; and
      a sensing component disposed on or within the substrate, wherein the sensing component has an impedance that loads the RF antenna, and wherein the impedance of the sensing component is dependent upon one or more sensed features.

2. The system of claim 1, further comprising:
   an RF reader, external to the contact lens, and configured to interrogate the RF antenna with an RF signal.

3. The system of claim 2, wherein the RF reader is further configured to receive a reflected RF signal from the RF antenna in response to interrogation.

4. The system of claim 3, wherein at least one of a magnitude, phase or frequency of the reflected RF signal is based, at least, on the impedance of the sensing component.

5. The system of claim 2, wherein the sensing component comprises a plurality of sensors.

6. The system of claim 5, wherein interrogation of the RF antenna with the RF signal comprises interrogation with at least one of a plurality of resonance frequencies, wherein at least one of the plurality of resonance frequencies is associated with at least one of the plurality of sensors.

7. The system of claim 6, wherein the RF reader is further configured to receive a reflected RF signal from the RF antenna in response to interrogation, wherein the reflected RF signal is associated with an impedance of at least one of the plurality of sensors.

8. The system of claim 1, wherein the sensing component comprises a capacitor.

9. The system of claim 1, wherein the sensing component comprises piezoelectric material.

10. A system, comprising:
    a contact lens, comprising:
       a substrate;
       a capacitive pressure sensing component disposed on or within the substrate, wherein the capacitive sensing component has an impedance dependent upon a sensed pressure; and
       a radio frequency (RF) antenna, loaded by the impedance of the capacitive pressure sensing component, and configured to reflect a modified version of a received RF signal at a selected frequency based, at least, on the sensed pressure.

11. The system of claim 10, wherein modification comprises modifying at least one of a magnitude, phase or frequency of the received RF signal.

12. The system of claim 10, further comprising:
    an RF reader, external to the contact lens, and configured to interrogate the RF antenna with the RF signal and detect a change in response of the RF antenna.

13. A method, comprising:
    sensing, by a sensing component of a contact lens, one or more sensed features, wherein the sensing changes an impedance of the sensing component, wherein the impedance of the sensing component loads an antenna in the contact lens; and
    reflecting, by the antenna, a radio frequency (RF) signal, wherein the RF signal is based, at least, on the impedance of the sensing component.

14. The method of claim 13, wherein at least one of the magnitude, phase or frequency of the reflected RF signal is based, at least, on the impedance.

15. The method of claim 13, further comprising:
receiving an interrogation signal, wherein the reflected RF signal is in response to receiving the interrogation signal.

16. The method of claim 13, wherein the sensing is performed via at least one of a temperature sensor or capacitive sensor.

17. The method of claim 13, wherein the sensing is performed via a sensing component comprising piezoelectric material.

18. The method of claim 13, wherein the sensing is performed via a sensing component comprising of a plurality of sensors.

19. The method of claim 18, further comprising:
receiving an interrogation signal, wherein the interrogation signal is associated with one of a plurality of resonance frequencies associated with one of the plurality of sensors.

* * * * *